(12) United States Patent
Gudladt

(10) Patent No.: US 7,897,090 B2
(45) Date of Patent: Mar. 1, 2011

(54) METHOD FOR FORMING A VESSEL-LOOP

(75) Inventor: Ralph Gudladt, Stuvenborn (DE)

(73) Assignee: Johnson & Johnson Medical GmbH, Hamburg-Norderstedt (DE)

( * ) Notice: Subject to any disclaimer, the term of this patent is extended or adjusted under 35 U.S.C. 154(b) by 521 days.

(21) Appl. No.: 11/840,625

(22) Filed: Aug. 17, 2007

(65) Prior Publication Data

US 2009/0048614 A1 Feb. 19, 2009

(51) Int. Cl.
*B28B 11/08* (2006.01)
*B29C 49/08* (2006.01)
*B29C 55/00* (2006.01)
*B29C 49/00* (2006.01)
*A61B 17/06* (2006.01)
*A61B 17/04* (2006.01)

(52) U.S. Cl. ............ 264/291; 264/159; 264/165; 264/248; 264/267; 264/271.1; 606/139; 606/226; 606/228; 156/165; 156/198; 156/212; 156/229; 156/294; 156/296; 156/308.2

(58) Field of Classification Search ............ 606/226, 606/190; 156/198
See application file for complete search history.

(56) References Cited

U.S. PATENT DOCUMENTS

| | | | | |
|---|---|---|---|---|
| 2,724,672 A | * | 11/1955 | Rubin | 156/287 |
| 2,983,639 A | * | 5/1961 | Jageman | 156/82 |
| 3,918,455 A | * | 11/1975 | Coplan | 606/225 |
| 4,251,310 A | * | 2/1981 | Goldhaber et al. | 156/274.8 |
| RE30,817 E | * | 12/1981 | Loyd et al. | 156/86 |
| 4,359,053 A | * | 11/1982 | Benjamin | 606/226 |
| 4,417,753 A | * | 11/1983 | Bacehowski et al. | 285/21.1 |
| 4,514,242 A | * | 4/1985 | MacLaughlin et al. | 156/73.5 |
| 5,021,043 A | | 6/1991 | Becker et al. | |
| 5,169,386 A | | 12/1992 | Becker et al. | |

(Continued)

FOREIGN PATENT DOCUMENTS

EP 1 127 561 B1 4/2005

(Continued)

OTHER PUBLICATIONS

F-C Riess et al., "A new method for coronary occlusion and local stabilization during minimally invasive LIMA-to-LAD bypass", European Journal of Cardio-thoracic Surgery, 15, (1999), 206-208.

(Continued)

*Primary Examiner*—Christina Johnson
*Assistant Examiner*—Benjamin Schiffman

(57) ABSTRACT

A vessel-loop having an elastic tube and a needle attached to one end thereof for use in various surgical procedures, and a method for forming same. The method includes the steps of positioning a heat-sensitive element within a section of elastic tubing, applying tensile forces to the opposed ends of the tubing section, and heating the heat-sensitive element and the portion of the tubing adjacent the heat-sensitive element so that the heat-sensitive element adheres to the adjacent tubing portion. The heat-sensitive element and the adjacent tubing portion are allowed to cool until a conjoined reduced-diameter portion is formed. The reduced-diameter portion is cut to form two ends, each having a reduced-diameter end. The reduced-diameter ends are then each secured to a needle, forming two vessel loops.

9 Claims, 4 Drawing Sheets

U.S. PATENT DOCUMENTS

| | | | |
|---|---|---|---|
| 5,403,345 A * | 4/1995 | Spingler | 606/224 |
| 6,083,188 A | 7/2000 | Becker | |
| 6,093,198 A | 7/2000 | Miyake | |
| 6,113,567 A | 9/2000 | Becker | |
| 6,238,364 B1 | 5/2001 | Becker | |
| 2004/0225250 A1 | 11/2004 | Yablonski | |
| 2006/0173482 A1 | 8/2006 | Melker | |

FOREIGN PATENT DOCUMENTS

| | | | |
|---|---|---|---|
| EP | 1 674 056 A1 | 6/2006 | |
| WO | WO 2006/076437 A2 | 7/2006 | |
| WO | 2006/076437 A3 | 2/2007 | |

OTHER PUBLICATIONS

Ethicon, Inc., "Ethiloop Silicone Sling—Instructions for use", Jan. 2004.

Quest Medical, Inc., Product information on "Vessel Occluding and Retracting Loops", as disclosed at http://www.questmedical.com/products/vessel_occluders.asp (2003).

Coroneo, Inc., Product description for "Cor-Vasc System (LG) with Large Retractor", as disclosed at http://www.coroneo.com/corvascsystem%20_large.htm (2005).

* cited by examiner

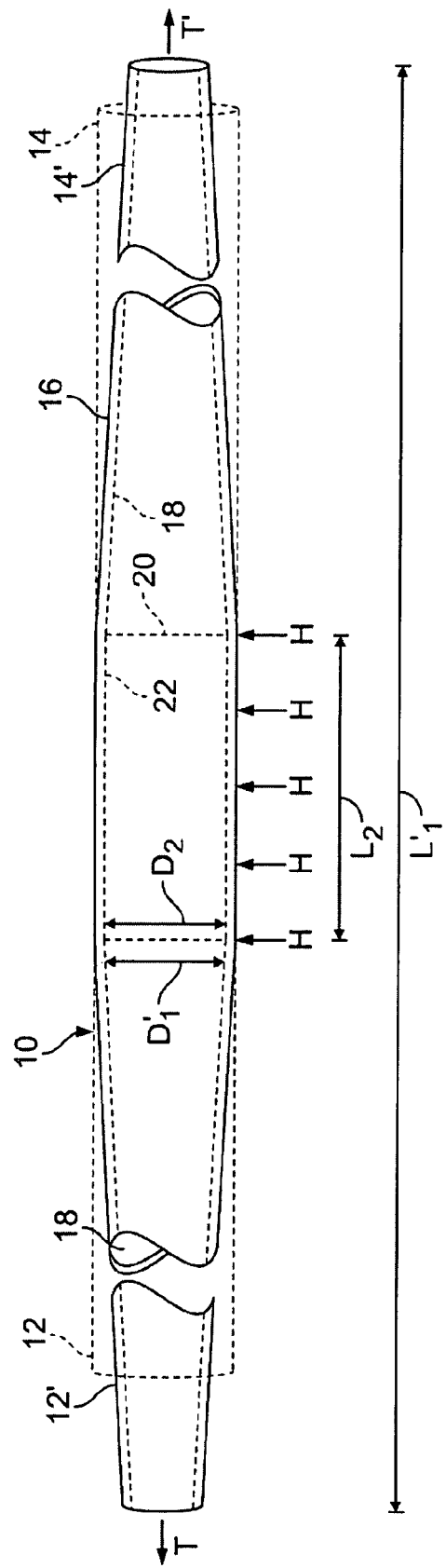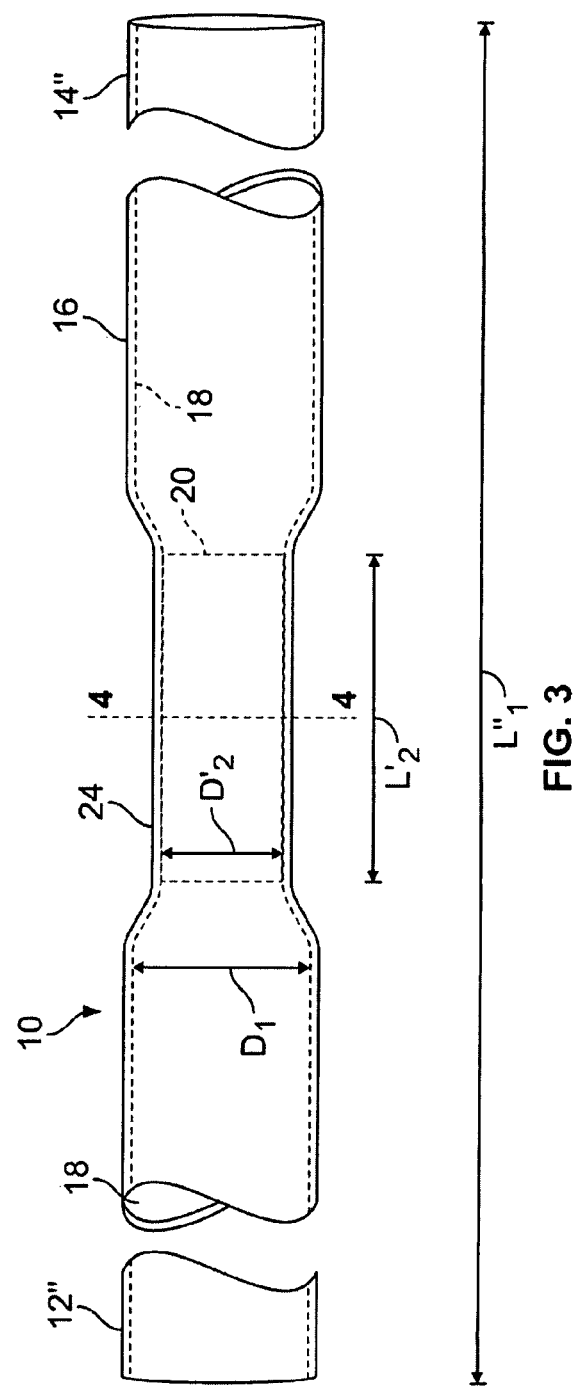

METHOD FOR FORMING A VESSEL-LOOP

FIELD OF THE INVENTION

This invention relates generally to a method of making vessel-loops for use in surgical procedures, and, more particularly, to a method of making vessel-loops including ends having a reduced-diameter end for insertion into an opening in a needle, such as a borehole.

BACKGROUND OF THE INVENTION

Vessel-loops, or vascular loops, are used by surgeons to occlude blood flow in blood vessels when performing a surgical anastomotic procedure (i.e., the surgical connection of two tubular structures, such as bypass surgery), and to hold or position an organ to facilitate or improve the visualization of a surgical site. Vessel-loops are used in different surgical procedures, including cardiovascular, thoracic vascular, orthopedic and urological surgery. A vessel-loop may include a hollow elastic tube having at least one end attached to a blunt pointed surgical needle. The elastic tube of the vessel-loop is hollow so that it flattens against the vessel when tension is applied, thereby providing a greater vessel surface-contacting area. The elastic tube is typically made of silicone rubber. The blunt pointed needle is used to guide the elastic tube through tissue. After the procedure is completed, the vessel-loops are removed from the patient.

Elastic silicone rubber tubes are also used in the manufacture of lacrimal stents, catheters and similar tubular devices used in dilating the lacrimal system. For example, these elastic tubes may be attached to a probe to introduce same into the nasal cavity of a patient (see, e.g., the devices disclosed in U.S. Pat. Nos. 5,169,386; 6,083,188; and 6,238,364).

Vessel-loops are typically manufactured using the following labor-intensive procedure. A length of hollow silicone rubber tubing is cut to form a silicone tube. A thin wire loop is used to manually pull the silicone tube into and through a section of hollow steel tubing which is later formed into a blunt pointed needle. A piece of catgut is then manually inserted into the silicone tube and manipulated therein so as to secure the silicone tube within the steel tube. The silicone tube is then pulled back so that one of its ends is positioned inside one end of the steel tube. This end of the steel tube is then closed using a Torrington machine, securing the end of the silicone tube thereto. The closed end is then manually ground and polished to form a blunt tip on the end of the steel tube distal to the silicone tube. The tip is then manually ground into a specified shape and polished. The resulting needle is then shaped so that a curve having a specified radius is formed. The silicone tube, which has been attached to the steel tube as it undergoes the foregoing processing steps to be formed into a needle, is then cut to a specified length. The silicone tube is then cleaned using alcohol, or another suitable solvent, and the needle is then siliconized. The resulting vessel-loop product may then be packaged, sterilized and distributed to end users (e.g., hospitals, etc.).

The manufacturing procedure described above presents several problems. One problem with this procedure is that the step of grinding the needle tip generates fusels and metallic debris, thereby making the procedure unsuitable for a "white area" abiding by good manufacturing practices ("GMPs") in connection with the manufacture of medical devices. For instance, the attachment of the silicone tube to the steel tube at an early stage of the procedure results in the undesired handling of the silicone tube during the later steps of forming the needle. The silicone tube is therefore exposed to the fusels and metallic debris generated later in the process. The metallic debris is especially problematic in that it adheres to the silicone tube.

The procedure described above also includes several tedious manual steps in the assembly of the needle, making it inefficient and costly. The pulling, threading and securing of the silicone tube in the steel tube is especially difficult, exacting and complicated. Moreover, while the above procedure requires the use of catgut to secure the silicone tube within the steel tube, some countries have imposed bans on the use of catgut in surgical applications.

Another shortcoming associated with the above procedure is that the silicone tubes may only be used with needles which are manufactured using this procedure. In other words, needles made using other methods may not be compatible with the silicone tubes. The use of this procedure is thus limited.

SUMMARY

A vessel-loop having an elastic tube and a needle attached to one end thereof for use in various surgical procedures is disclosed, as well as a method for forming the vessel-loop. The method includes the steps of (1) positioning a heat-sensitive element within a section of tubing intermediate first and second opposed ends of the tubing section, the tubing section having an inner surface defining a first diameter, and the heat-sensitive element having an outer surface defining a second diameter which is less than the first diameter; (2) applying a first tensile force to the first end of the tubing section and applying a second tensile force to the second end of the tubing section, the first and second forces acting in generally opposite directions so as to decrease the diameter of the tubing section from the first diameter to the second diameter, whereby the inner surface of an adjacent portion of the tubing section is brought into contact with the outer surface of the heat-sensitive element; (3) applying heat to the heat-sensitive element and the adjacent portion of the tubing section, whereby at least the outer surface of the heat-sensitive element melts and adheres to the adjacent portion of the tubing section; (4) allowing the heat-sensitive element and the adjacent portion of the tubing section to cool to a point where a conjoined reduced-diameter portion is formed; (5) dividing the reduced-diameter portion so as to form two ends having respective reduced-diameter ends; and (6) securing the reduced-diameter end of one of the ends within an opening formed in a needle, such as a borehole or a channel.

The aforementioned dividing step may be performed by different techniques, including cutting the reduced-diameter portion so as to form two ends. Such cutting may be performed in a direction transverse to the axis of the tubing section.

BRIEF DESCRIPTION OF THE DRAWINGS

For a better understanding of the present invention, reference is made to the following detailed description of various exemplary embodiments considered in conjunction with the accompanying drawings, in which:

FIG. 2 is a schematic illustration of a section of tubing on which tensioning is applied and a heating step is being initiated in accordance with the method of the present invention;

FIG. 3 is a schematic illustration of the tubing section after the steps illustrated in FIG. 2 have been completed;

DETAILED DESCRIPTION

As discussed in the Background section, diverse medical devices utilize and/or incorporate silicone rubber tubes which are attached to a needle or a probe and passed through bodily tissues. While the use of silicone rubber tubes in the manufacture of vessel-loops is discussed exclusively hereinbelow, it is understood that the method of the present invention may be applied in the manufacture of other medical devices, including the aforementioned lacrimal stents.

Before explaining the present invention in detail, it should be noted that the invention is not limited in its application or use or to the details of construction and arrangement of parts illustrated in the accompanying drawings and description. The invention as illustrated may be implemented or incorporated in other embodiments, variations and modifications, and may be practiced or carried out in various ways.

Figure 1:
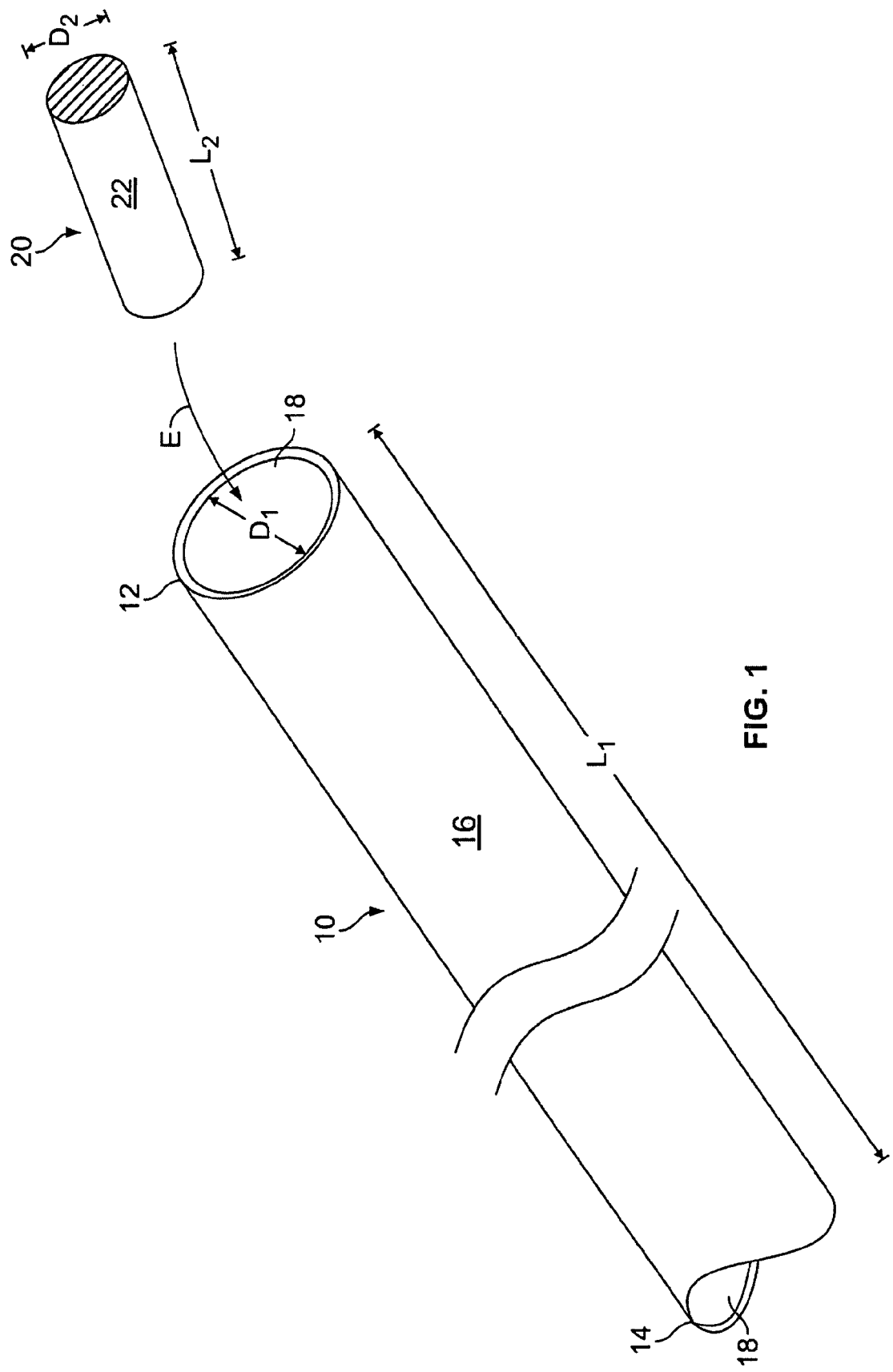
FIG. 1 is an exploded perspective view of a length of tubing and a heat-sensitive element at the outset of the method of the present invention, wherein the heat-sensitive element is to be inserted into the length of tubing.

Steps of the inventive method for making the vessel-loop are illustrated in FIGS. 1-5. As shown in FIGS. 1-3, the tube of the vessel-loop is formed from an elongated section of silicone rubber tubing 10 having opposed ends 12, 14, an outer surface 16 and an inner surface 18. The tubing section 10 has a length $L_1$ and an inner diameter $D_1$.

Reference is made to FIG. 1, in which a solid, cylindrical heat-sensitive element 20 having an outer surface 22, a length $L_2$ and an outer diameter $D_2$ is introduced into the end 12 of the tubing section 10, as illustrated by the arrow E. The length $L_2$ and outer diameter $D_2$ of the heat-sensitive element 20 are less than the length $L_1$ and inner diameter $D_1$, respectively, of the tubing section 10. While the outer diameter $D_2$ is less than the inner diameter $D_1$, the diameters are selected such that the outer surface 22 of the heat-sensitive element 20 is spaced from, but close to, the inner surface 18 of the tubing section 10. The heat-sensitive element 20 is preferably made of polypropylene in this embodiment.

Referring now to FIG. 2, once the heat-sensitive element 20 has been inserted into the tubing section 10, it is positioned therein so as to be intermediate the ends 12, 14, and, for example, approximately equidistant therefrom. Axial tension is then applied to the ends 12, 14 in opposite directions, as indicated by arrows T, T', respectively, thereby axially stretching the tubing section 10, and resulting in stretched, or tensioned ends 12', 14'. The application of axial tension T, T' reduces the inner diameter $D_1$ of the tubing section 10, and elongates the tubing section 10 from $L_1$ to $L'_1$. Specifically, the inner diameter $D_1$ of the tubing section 10 is reduced to a smaller inner diameter $D'_1$, which is the same as (i.e., equal to) the outer diameter $D_2$ of the heat-sensitive element 20 along the length $L_2$, and the same as (i.e., equal to) or less than the outer diameter $D_2$ along the remaining length $L'_1$. The inner surface 18 of the tubing section 10 is thus brought into contact with the outer surface 22 of the heat-sensitive element 20. The inner diameter $D'_1$ of the tubing section 10 is initially smallest at the stretched ends 12', 14', where the axial tension T, T' is applied. Phantom lines are used to illustrate the comparative position, size and shape of the unstretched ends 12, 14 relative to the stretched ends 12', 14' in FIG. 2.

Still referring to FIG. 2, heat H is then applied to the heat-sensitive element 20 through the adjacent portion of the tensioned tubing section 10. More particularly, a duct or vent (not shown) provides a hot air stream along the length $L_2$ of the heat-sensitive element 20. The temperature of the hot air stream typically ranges from 180° C. to 280° C. Since the approximate melting temperature of polypropylene is 165° C., the heat H causes the outer surface 22 of the heat-sensitive element 20 to soften and melt, at least partially. On the other hand, since the melting temperature of silicone rubber is in excess of 300° C., the tubing section 10 does not melt in response to the heat H. As a result of the heat H, the polypropylene along the outer surface 22 of the heat-sensitive element 20 melts and adheres to the adjacent portion of the inner surface 18 of the tubing section 10. As the heat-sensitive element 20 melts and is subjected to the axial tension T, T', its length increases from $L_2$ to $L'_2$, and its diameter decreases from $D_2$ to $D'_2$ (see FIG. 3).

Referring now to FIG. 3, once a secure connection is formed between the outer surface 22 of the heat-sensitive element 20 and the inner surface 18 of the tubing section 10, the heat H is removed, and the heat-sensitive element 20 and the adjacent portion of the tubing section 10 are allowed to cool to room temperature. A stream of cool air from a compressor (not shown) provided by an air gun (also not shown) along the length $L'_2$ of the heat-sensitive element 20 may also be used to expedite the cooling step. Once the polypropylene heat-sensitive element 20 has been allowed to solidify and stabilize, the axial tension T, T' is removed from the stretched ends 12', 14' respectively, of the tubing section 10, resulting in ends 12", 14" which have substantially returned to an unstretched position, size and shape. The tubing section 10 now has a length $L''_1$ which is slightly longer than its pre-stretched length $L_1$. The result of the process thus far is to produce a reduced-diameter portion 24 of the tubing section 10 along the length $L'_2$ of the heat-sensitive element 20. More particularly, the reduced-diameter portion 24 includes the heat-sensitive element 20 and the surrounding, attached portion of the tubing section 10 which has the smaller inner diameter $D'_1$ than both the outer diameter $D_2$ and the inner diameter $D_1$ of the remainder of the tubing section 10. The reduced-diameter portion 24 has a length substantially equal to the length $L'_2$ of the heat-sensitive element 20. The mechanical connection between the heat-sensitive element 20 and the adjacent tubing section 10 formed by the foregoing steps is stable because the heat-sensitive element 20 secures the tubing section 10 of the reduced-diameter portion 24 in place and prevents it from expanding and returning to its original inner diameter $D_1$.

Figure 4:
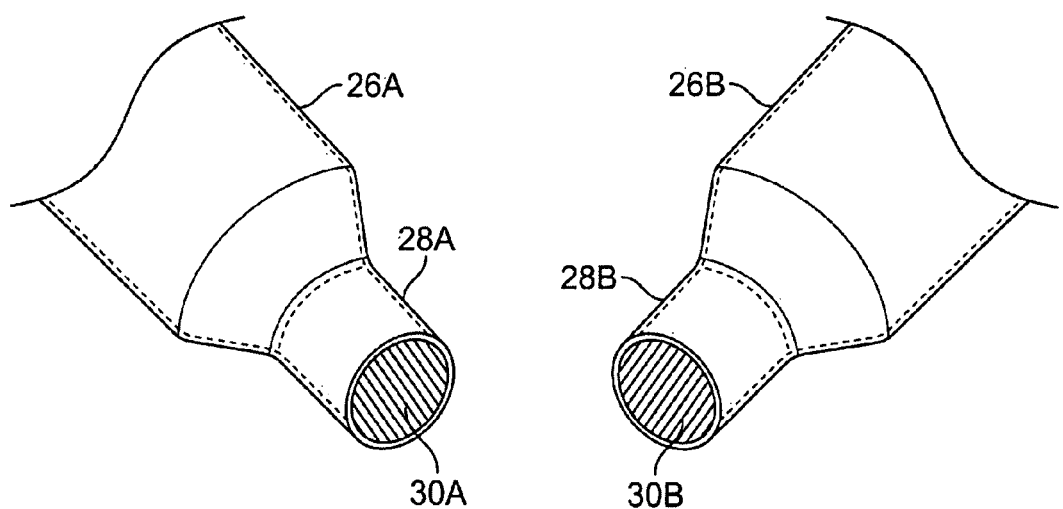
FIG. 4 is a perspective view of two reduced-diameter ends formed by cutting the tubing section of FIG. 3 along line 4-4 in FIG. 3.

Still referring to FIG. 3, after the reduced-diameter portion 24 has been formed, it is cut in a direction transverse to a longitudinal axis of the tubing section 10 (i.e., along line 4-4). The cutting step yields two ends 26A, 26B each having one reduced-diameter end 28A, 28B, respectively, as illustrated in FIG. 4. Prior to the cutting step, the reduced-diameter ends 28A, 28B formed the conjoined segments of the reduced-diameter portion 24 (see FIG. 3). The portions of the heat-sensitive element 20 within each end 26A, 26B form solid cores 30A, 30B, respectively, within the reduced-diameter ends 28A, 28B. The reduced-diameter ends 28A, 28B may then be inserted into a needle opening, facilitating the attachment of the ends 26A, 26B to needles in the formation of vessel-loops, as discussed further hereinbelow.

To form a reduced-diameter end of a tube suitable for insertion into a given needle opening, it is helpful to establish operating parameters that will result in a reduced diameter that is slightly smaller than that of the needle opening. To achieve this, a relationship may be established between the starting length $L_2$ of the heat-sensitive element 20 and the desired outside diameter of the reduced-diameter end 30A. For example, the following predictive formula was determined for when the heat-sensitive element 20 is made from polypropylene (metric size 4 PROLENE suture manufactured by Ethicon, Inc.) and the tubing section 10 is made of silicone tubing (1.2 mm diameter, catalog number 4660112 from Raumedic AG, D95233 Helmsbrecht, Germany):

$$y_i = 1.419 \cdot y_o \cdot x^{-2.284}$$

where:

x is the measurement of the desired outer diameter of the reduced-diameter portion 24 of the silicone tubing section 10;

$y_o$ is the measurement of an initial length $L_1$ of the silicone tubing section 10 before it is subjected to the axial tension T, T' (i.e., stretched) and the heat H is applied; and $y_i$ is the measurement of the target length $L_1'$ of the length $L_1$ of the silicone tubing section 10 after it is subjected to the axial tension T, T' (i.e., stretched) and the heat H is applied. This is the length an operator should use when stretching the tubing section 10 in order to achieve the desired outer diameter measurement x.

This relationship was derived for the heat-sensitive element 20 and tubing section 10 of the present embodiment, as discussed above. Other relationships may be derived for other combinations of heat-sensitive elements and elastic tubes, and those made of different materials.

Figure 5:
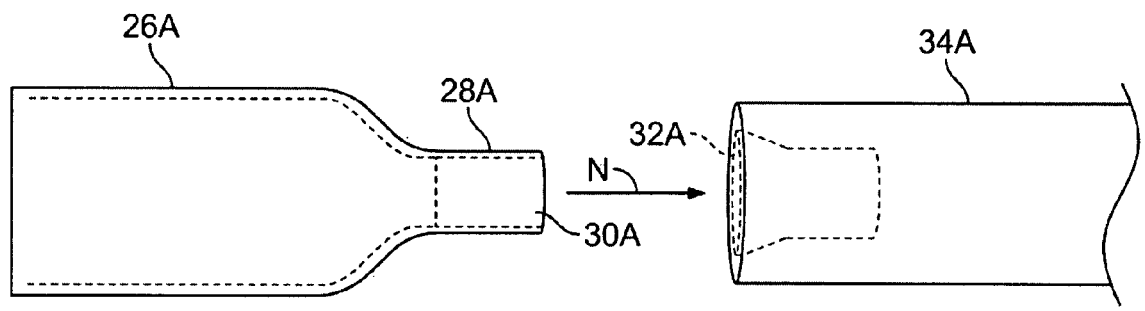
FIG. 5 is an exploded view showing one of the reduced-diameter ends of FIG. 4 and its relationship to a needle as they are being combined to form a vessel-loop in accordance with the method of the present invention.

With reference now to FIG. 5, only one end 26A is shown, for the sake of clarity, with the understanding that the other end 26B is formed and operates in the same way. The reduced-diameter end 28A of the end 26A is dimensioned to be inserted into a borehole 32A of a blunt pointed needle 34A. The needle 34A has been machined and completed prior to attaching the end 26A thereto. The reduced-diameter end 28A is inserted into the borehole 32A, as illustrated by the arrow N. The borehole 32A of the blunt pointed needle 34A is then crimped, or swaged, to secure the reduced-diameter end 28A therein, further securing the core 30A within the reduced-diameter end 28A. Needles having other types of openings may also be utilized with the reduced-diameter end 28A, as discussed below.

Figure 6:
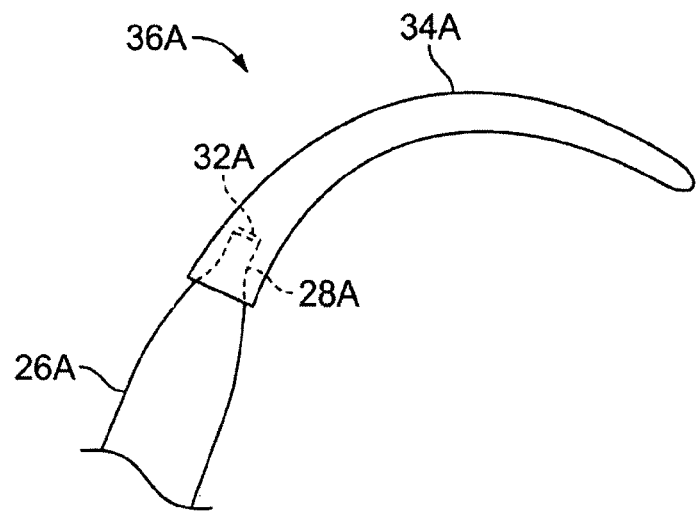
FIG. 6 is a side view of the needle end of the vessel-loop illustrated in FIG. 5, once it has been assembled according to the method of the present invention.

Reference is now made to FIG. 6, which illustrates the needle end of a vessel-loop 36A formed by the method of the present invention. The vessel-loop 36A includes the needle 34A and the end 26A, the reduced-diameter end 28A of which has been secured in the borehole 32A of the needle 34A. Following the attachment of the end 26A to the needle 34A, the vessel-loop 36A is packaged, sterilized and distributed to end users (e.g., hospitals, etc.) A similar procedure would be followed to form a vessel-loop 36B (see FIG. 7) having a needle (not shown) joined to the end 26B.

Figure 7:
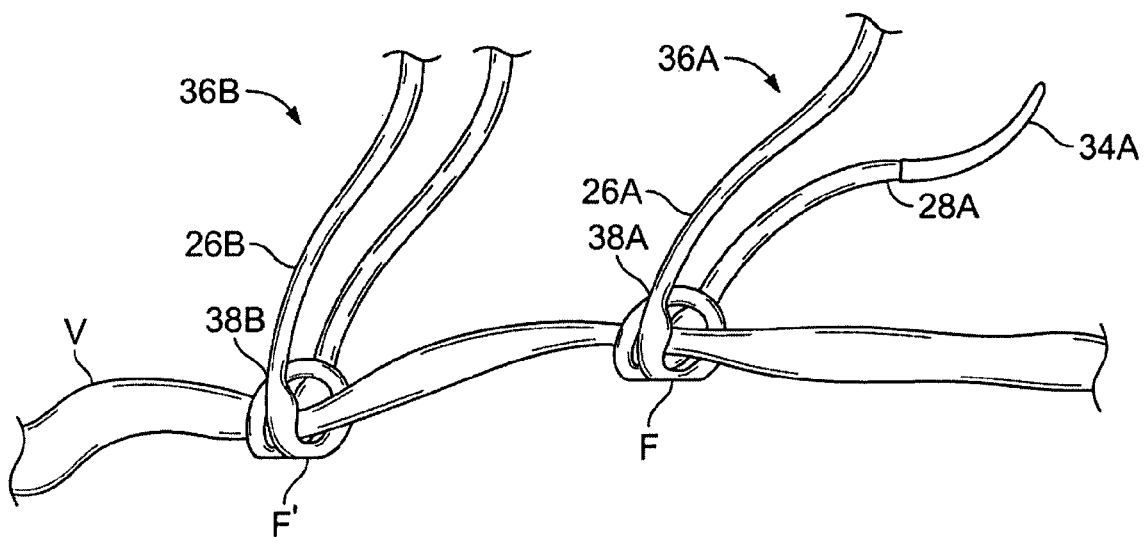
FIG. 7 is a partial perspective view of two vessel-loops manufactured in accordance with the method of the present invention, as they are being used to occlude a blood vessel during the performance of a surgical procedure.

Referring now to FIG. 7, two vessel-loops 36A, 36B are positioned about a blood vessel V to occlude blood flow during a surgical procedure. The vessel-loop 36B is shown as being suspended from above the surgical site. A stabilizer platform (not shown) may be arranged during the preliminary steps of the surgical procedure and used to support the suspended vessel-loop 36B. The needle 34A and adjoining reduced-diameter end 28A of the vessel-loop 36A have been threaded through the tissue of the patient, but have not yet been returned to a vertical orientation for suspension thereof. Tubular portions 38A, 38B of the vessel-loops 36A, 36B respectively, flatten at locations F, F' where they contact and are looped about the blood vessel V, thereby increasing their contact area with the blood vessel V to facilitate occlusion of the blood vessel V during surgery.

The tube with a reduced-diameter end formed by the present method may also be attached to other types of needles. For instance, a channel needle is formed by cutting a longitudinal channel in the end of the needle opposite the point. The reduced-diameter end is inserted into the channel, and the side walls of the needle surrounding the channel are then curled, or rolled, toward each other to compress the reduced-diameter end therein. Alternatively, the walls may be rolled together prior to the insertion of the reduced-diameter end and connected to each other by a seam, creating a round opening on the end of the needle opposite the point. The reduced-diameter end is then inserted into the opening and secured therein. In addition to being suitable for use with needles having different attachment geometries, this invention is also suitable for use with needles having different point geometries. For example, needle points may taper to a point, may be tapered to a point with small cutting edges, may include cutting edges such as with reverse or conventional cutting needles, may be spatulated as with some needles used in ophthalmology, or may have any other type of point geometry.

One of the most significant advantages of the procedure described above is the separation of the needle and the tube during the manufacture and processing of each. More particularly, the tube has not been attached to the needle when it is undergoing sharpening, grinding, etc. As a result, the tube is not exposed to metallic debris from the needle-related operations. In such circumstances, no additional cleaning steps are necessary. Furthermore, the difficult and time-consuming steps of securing the tube within the needle using wire loop, catgut, etc. are eliminated using the method of the present invention.

Besides the modifications discussed above, additional modifications can be implemented in the inventive manufacturing method described hereinabove. For instance, the heat-sensitive element may alternatively be made of another plastic material having similar properties, such as polyethylene. The tubing section and the tube may also be formed of any suitable biocompatible material which is sufficiently elastic and flexible.

It should be understood that the embodiment described herein is merely exemplary and that a person skilled in the art may make many variations and modifications thereto without departing from the spirit and scope of the present invention. All such variations and modifications, including those discussed above, are intended to be included within the scope of the invention as defined in the appended claims.

I claim:

1. A method for forming a vessel-loop, comprising:
  positioning a heat-sensitive element within a section of tubing intermediate first and second opposed ends of the tubing section, the tubing section having an inner surface defining a first diameter, and the heat-sensitive element having an outer surface defining a second diameter which is less than the first diameter;
  applying a first tensile force to the first end of the tubing section and applying a second tensile force to the second end of the tubing section, the first and second forces acting in generally opposite directions so as to decrease the diameter of the tubing section from the first diameter to the second diameter, whereby the inner surface of an adjacent portion of the tubing section is brought into contact with the outer surface of the heat-sensitive element;

applying heat to the heat-sensitive element and the adjacent portion of the tubing section, whereby at least the outer surface of the heat-sensitive element melts and adheres to the adjacent portion of the tubing section;

allowing the heat-sensitive element and the adjacent portion of the tubing section to cool to a point where a conjoined reduced-diameter portion is formed;

dividing the reduced-diameter portion so as to form two ends having respective reduced-diameter ends; and securing the reduced-diameter end of one of the ends within an opening formed in a needle.

2. The method of claim 1, wherein said securing step is performed by crimping the needle with the reduced-diameter end of the tube inside the needle opening.

3. The method of claim 1, wherein said dividing step includes cutting the reduced-diameter portion so as to form two ends.

4. The method of claim 3, wherein said cutting is performed in a direction transverse to a longitudinal axis of the tubing section.

5. The method of claim 1, wherein said step of applying heat to the heat-sensitive element and the adjacent portion of the tubing section includes providing a hot air stream.

6. The method of claim 1, wherein said step of allowing the heat-sensitive element and the adjacent portion of the tubing section to cool includes directing a cool air stream onto the reduced-diameter portion.

7. The method of claim 1, wherein the tubing section is cut from an elastic material.

8. The method of claim 7, wherein the elastic material is silicone rubber.

9. The method of claim 1, wherein the heat-sensitive element is made of polypropylene.

* * * * *